(12) United States Patent
Wennemann

(10) Patent No.: US 6,537,067 B1
(45) Date of Patent: Mar. 25, 2003

(54) DEVICE TO TREAT THE TEETH ADJACENT TO A GAP FOR THE PLACEMENT OF A DENTAL BRIDGE

(76) Inventor: Ulrich Wennemann, Beroldingerstrasse 5a, Umkirch (DE), D-79224

(*) Notice: Subject to any disclaimer, the term of this patent is extended or adjusted under 35 U.S.C. 154(b) by 0 days.

(21) Appl. No.: 09/680,084

(22) Filed: Oct. 5, 2000

(30) Foreign Application Priority Data

Oct. 6, 1999 (DE) .......................... 199 48 393

(51) Int. Cl.[7] .................................................. A61C 3/02
(52) U.S. Cl. ...................................................... 433/76
(58) Field of Search .................................... 433/76, 75

(56) References Cited

U.S. PATENT DOCUMENTS

| | | | |
|---|---|---|---|
| 1,407,840 A | * 2/1922 | Cruttenden | 433/76 |
| 2,634,501 A | 4/1953 | Linet | 433/76 |
| 3,011,259 A | 12/1961 | Baum | 433/75 |
| 5,934,907 A | 8/1999 | Marshall | 433/181 |

FOREIGN PATENT DOCUMENTS

DE 684665 12/1939

* cited by examiner

*Primary Examiner*—John J. Wilson
(74) *Attorney, Agent, or Firm*—Volpe and Koenig, P.C.

(57) ABSTRACT

A device (1) to treat the teeth (2) adjacent to a gap (3) for the purposes of placing a dental bridge (4) that replaces at least one missing tooth has a treatment tool (5) to remove tooth material, in particular a grinding tool. The device (10 has a mounting fixture (6) to fasten to the teeth of the patient that contains an adjustable positioning device (7) to position the treatment tool (5). By means of the positioning device (7), the treatment tool (5) can move back and forth toward the neighboring teeth (2) to make recesses (8) in the sides of the teeth (2) facing the gap (3).

6 Claims, 5 Drawing Sheets

DEVICE TO TREAT THE TEETH ADJACENT TO A GAP FOR THE PLACEMENT OF A DENTAL BRIDGE

BACKGROUND

This invention is directed to a device to treat the neighboring teeth to a gap in the teeth for placement of a dental bridge that replaces at least one missing tooth. Included is a treatment tool to remove the tooth material, in particular a grinding tool, and a mounting fixture that is fastened to the patient's teeth, to which an adjustable positioning device is attached to position the treatment tool. This mounting fixture has a sliding guide with a sled that shifts relative to the mounting fixture and guide rails or guide pins that guide the treatment tool.

From DE-PS 684 665, a device of this general type is already known, in which a drag bearing is located between the mounting fixture and the sliding guide. With the help of this drag bearing, the sliding guide is connected to the mounting fixture and tilts about a pivot axis oriented approximately at right angles to the plane of the chewing surface of the teeth with the device in the working position. The drag bearing has a pivot axis solidly connected to the mounting fixture on which a bushing is located which rotates and shifts axially. The sliding guide is connected to the bushing.

To install a dental bridge, the device is first fastened to the patient's teeth using the mounting fixture. Then, the teeth neighboring the gap to be bridged are ground with the device and brought to a form that is suitable for an anchoring of the dental bridge to the neighboring teeth. During this, the treatment tool is guided exactly parallel at the sled. The form in which the neighboring teeth are brought is dependent on the form of the anchoring elements provided for the dental bridge.

Then, holes are made in the teeth neighboring the gap to be bridged to set in pins that serve to anchor the dental bridge. To this end, the treatment tool guided by the sled is first placed in the position of the neighboring tooth provided for its respective hole, wherein the sled is tilted and/or shifted with respect to the mounting fixture into the respective position. Then, the treatment tool is sunk into the tooth material to make the hole by shifting the bushing to which the sliding guide is fastened along the pivot axis accordingly.

After all holes have been prepared, the pins are placed into the holes and with the help of a hardened dental impression material, an impression of the patient's teeth is taken. The paste-like or doughy dental impression material is filled into a strip that is U-shaped in cross section adjusted to fit the patient's teeth. This strip is then placed with the dental impression material contained therein onto the patient's teeth. After the dental impression material is hardened to a solid but still flexibly deformable mass in the oral cavity, the strip is pulled out with the dental impression material from the patient's teeth. A temporary filling is placed in the ground and drilled neighboring teeth that protects them from damage until the dental bridge is installed.

With the help of the dental impression, a dental technician prepares a model of the patient's teeth in the laboratory. A hardening material is filled into the negative form of the dental impression, which later forms the model, for example plaster of Paris. After the model hardens, the dental impression is pulled from the model and the dental bridge is manually prepared using the model. In this manner, the form of the anchoring elements of the dental bridge is individually and as exactly as possible adjusted to the form of the ground neighboring teeth.

The dental bridge thus prepared is then installed. The temporary filling is removed and then the dental bridge is placed with its anchoring elements onto the teeth neighboring the gap.

This prior-known device has the disadvantage in that it requires a number of processing steps to place and prepare the dental bridge. In particular, a dental impression must be taken and a model of the teeth must be made after making the holes in the neighboring teeth serving to anchor the dental bridge. Also, the dental bridge must be prepared using expensive manual activity and adjusted according to the model. It is also adverse that the manufacture and adjustment of the dental bridge to fit the neighboring teeth treated in advance using the device is so time-intensive that the patient must appear for at least two visits to the dentist. In the first visit, the teeth being used for the anchoring of the dental bridge are ground and the dental impression is taken, whereas in the second visit the dental bridge is placed and anchored to the neighboring teeth.

SUMMARY

The object is therefore to create a device of the type mentioned above that enables simple, quick and economical treatment of the patient. In particular, the device is to enable careful treatment of the teeth being used for the anchoring of the dental bridge, wherein as much tooth material as possible is to be retained.

This object is met by the invention having the features of patent claim 1. Using the mounting fixture, the treatment tool can be positioned with a higher precision at the teeth used to anchor the dental bridge that are adjacent to the gap. The mounting fixture is fixed on both sides of the gap to the teeth located there, resulting in a correspondingly stabile connection of the carriage to the teeth. Since the guide pins require only relatively little space, the gap is easy to access, opening up the view of the sled and, if necessary, the treatment tool. This allows the dentist to observe the material removal when making the recesses in the neighboring teeth. The treatment tool located in the working position can be moved toward and away from the neighboring teeth by shifting the sled toward the sides of these teeth facing the gap. In this way, notch-shaped recesses can be made in the teeth adjacent to the gap in a simple manner. Anchoring protrusions on the dental bridge shaped to fit these recesses can then be placed into them. Making the recesses provided for the anchor protrusions in the neighboring teeth can, for example, be done using a rotating grinding or cutting tool, using a laser and/or using a sandblasting device. On the one hand, this enables particularly careful treatment of the neighboring teeth, with the removal of only that tooth material actually needed to anchor the dental bridge, the remaining tooth substance otherwise being retained. On the other hand, however, a very exact, predetermined geometry is attained of the positions to be treated on the neighboring teeth using the device. This makes it possible to manufacture the dental bridge prior to the treatment of the neighboring teeth and to then make the recesses for anchoring the dental bridge in the teeth neighboring the gap, with dimensions matching the anchor positions of the dental bridge. In an advantageous manner, this allows the time-consuming and expensive preparation of a dental bridge and a model of the patient's teeth to be done away with, which makes the installation of the dental bridge easy and quick. In this way, in particular, it is possible to place the dental bridge right after the recesses are made in the neighboring teeth provided to anchor the dental bridge so that the entire treatment can be performed in only one sitting. For the patient, this has the main advantage in that the installation of a temporary filling to protect the treated surfaces of the neighboring teeth is done away with and that full functioning and utility of the patient's teeth is restored after a short time. Moreover, time-consuming manual adjustment of the anchoring positions of the dental bridge to the neighboring teeth and recesses made in them also is eliminated, which enables a more economic manufacture of the dental bridge.

It is advantageous if stops are provided on the mounting fixture to limit the positioning path of the treatment tool in the direction that the sled slides on both sides of the sled. The recesses for the anchor protrusions of the dental bridge provided on both sides of the gap can then be made in the lateral surfaces of the neighboring teeth adjacent to the gap with a defined distance between their base surfaces.

It is advantageous if the mounting fixture has at least one U-shaped holder in the form of a fork that grips at least one of the patient's teeth in the working position, in particular a tooth adjacent to the gap. This makes the holder especially easy to fasten to the teeth neighboring the gap. The sides of the U-shaped holders can be designed if necessary as a clamping arm, between which the tooth being used to fasten the holder can be clamped.

In an especially advantageous embodiment of the invention, a hardening and/or solidifying compound is provided to coat the interior cavity of the U-shaped holders. This is preferably paste-like or doughy in the pre-installed position of the holder so that the holder can be easily placed onto a tooth of the patient after its interior cavity has been coated with the compound. In the working position, the compound located in the intermediate space between the tooth and the carriage solidifies or hardens so that the holder is then solidly connected to the tooth. Preferably, the compound in the solidified condition still has a certain level of elasticity so that the holder and its compound can be pulled off of the patient's teeth after treating the teeth adjacent to the gap. The compound is preferred to be a silicon compound. However, it can also be a dental impression material. The carriage can be perforated on its inside facing the compound or can have a structure that enables better adhesion of the compound to the mounting fixture in the working position or so that it and the compound can be pulled off of the tooth after the compound hardens. To this end, the compound is placed in the mounting fixture just prior to placing the mounting fixture onto the patient's teeth.

It is advantageous if the treatment tool is located at the tool head of dental treatment equipment and if this tool head can be attached removably to the sled of the sliding guide. This makes it possible to adapt the sled guided by the mounting fixture to fit dental treatment equipment already in existence in dental practice in a simple manner so that the existing equipment can continue to be used and its functionality can be increased.

To this end, the sled has a receptacle adjusted to fit the form of the tool head of the dental treatment equipment, into which the tool head can be placed in a form-fit manner. The receptacle is preferred to form a press fit with the tool head. The tool head can then be inserted in a simple manner onto the sled to connect to the sled and after the treatment is finished can again be pulled off of it.

It is advantageous if the tool head is designed as an angled head with a treatment tool rotating about a rotating axis, and if the tool head is connected to the carriage and can tilt about the rotating axis of the treatment tool relative to the carriage by means of a pivoting joint. The tool head can in this way be better positioned within the oral cavity of the patient. To this end, the pivoting joint is located on the sled of the sliding guide.

In a preferred embodiment of the invention, it is provided that the sliding guide has at least one guide rail to guide the sled fixed to the mounting fixture laterally on both sides of the sled and that the guide rails engage into a common annular notch located in the external perimeter of the sled or into a number of annular notch sections located in exterior perimeter areas of the sled diametrically opposite to one another so that the sled can be slid and rotated. In this way, an especially compact arrangement results that enables a good view of the gap and the areas to be treated of the adjacent teeth when it is in the working position. The tool head containing the treatment tool is slid and pivoted by means of the mounting fixture. The annular notch sections located at the exterior perimeter of the sled are preferred to extend along a common circle.

It is especially advantageous if the mounting fixture has at least two points of support located at a distance from one another along the direction of extension of the mounting fixture for the chewing surfaces of at least one tooth to be connected to the mounting fixture, and if at least one of these points of support is located on a spacing element that is adjustable perpendicular to the plane of the chewing surfaces relative to the positioning device. The distance of the positioning device from the teeth is then adjustable using the spacing element, for example to be able to adjust the mounting fixture to different tooth heights. To this end, an adjusting screw is provided as the spacing element that enables a continuous height or tilt adjustment of the positioning device relative to the plane of the chewing surface of the teeth.

The device according to the invention is especially advantageous if it is part of a kit to produce a dental bridge, wherein the kit has at least one pre-manufactured dental bridge with a bridge section and wherein the dental bridge has at least one anchor protrusion with prescribed dimensions in the direction of extension on both sides of the bridge section. The device contained in the kit to treat the teeth adjacent to the gap by making recesses in the lateral surfaces of the teeth adjacent to the gap, is designed such that the dimensions of the recesses correspond to those of the anchor protrusions of the dental bridge. This can be done in particular by providing the device used as the treatment tool with a rotating grinder or cutting tool that can move toward the lateral surfaces of the neighboring teeth parallel with its rotating axis and that has a diameter equal to the width of the anchor protrusions or somewhat larger than them. The dimensions of the recesses then fit those of the anchor protrusions so that they can be placed into the neighboring teeth right after the recesses are made. In this way, on one hand fast and economical installation of the dental bridge in the oral cavity results, and on the other hand, the pre-manufactured dental bridge can be manufactured as a standard part with prescribed dimensions, thus making its manufacture economical. The bridge section can a have at least one synthetic tooth.

It is advantageous if the anchor protrusions located on both sides of the bridge section have at least one equal dimension. The recesses to be made in the neighboring teeth to fasten the anchor protrusions can then also have one or more equal dimension or dimensions, which enables simple manufacture of the recesses and a correspondingly simple design of treatment equipment. Preferably, the anchor protrusions located on both sides of the bridge section have at least the same width in the plane of the chewing surfaces or a plane parallel to it perpendicular to the direction of extension of the dental bridge. The length of the anchor protrusions oriented in the direction of extension of the dental bridge can be different for the anchor protrusions located on either side of the bridge section, for example if one of the anchor protrusions is to be fastened to a premolar and the other is to be fastened to a molar.

To this end, the lateral abutting surface of the anchor protrusion opposite the bridge section lies on a cylindrical surface or an outer conical surface of a truncated cone that narrows as it goes from the chewing surface of the synthetic tooth to the base of the tooth. The recesses in the neighboring teeth to place the anchor protrusions can then be manufactured in a simple manner using cylindrical or conical processing tools common in dental practice.

In an advantageous embodiment of the invention, at least one anchor protrusion is formed by the free end of a locking pin placed in a hole of the dental bridge and/or is connected in one piece to the bridge section. The locking pin can penetrate a hole in the dental bridge, with the free ends of the locking pin protruding from the bridge section on both sides forming the anchor protrusions. However, the anchor protrusions can also be designed in one piece with the bridge section, for example, as a complete ceramic part. The dental bridge then has a high bending and fracture resistance.

It is especially advantageous if the kit has a number of pre-manufactured dental bridges with synthetic teeth of different colors, materials and/or dimensions. The dentist can then select a dental bridge from the kit that fits the individual dimensions of the gap and/or the neighboring teeth and install it for the patient after the recesses are made to anchor the dental bridge. For dental bridges whose color is patterned according to natural teeth, such as dental bridges made of ceramic or plastic blends with a support structure made of gold, the kit can even have dental bridges with different colors so that the dentist can select a dental bridge whose color exactly matches the color of the patient's teeth.

It is especially advantageous if the kit has dental bridges made of different materials, for example dental bridges whose synthetic teeth are made completely of one noble metal such as gold and/or dental bridges in which the synthetic teeth are blended with plastics or ceramics. In this way, it is possible to place temporary dental bridges made of different materials for the purposes of trial after the recesses in the neighboring patient's teeth are made to anchor the dental bridge. The patient can then test the appearance of different dental bridges. The patient can then decide whether he would prefer to have, for example a low-cost dental bridge made of gold or would rather have a more optically pleasing but also more expensive dental bridge with ceramic-layered synthetic teeth whose color more closely resembles that of the natural teeth.

BRIEF DESCRIPTION OF THE DRAWINGS

The preferred embodiments of the invention are explained in more detail below in connection with the accompanying drawings. Some figures show more schematic detail.

DETAILED DESCRIPTION OF THE PREFERRED EMBODIMENTS

Figure 1:
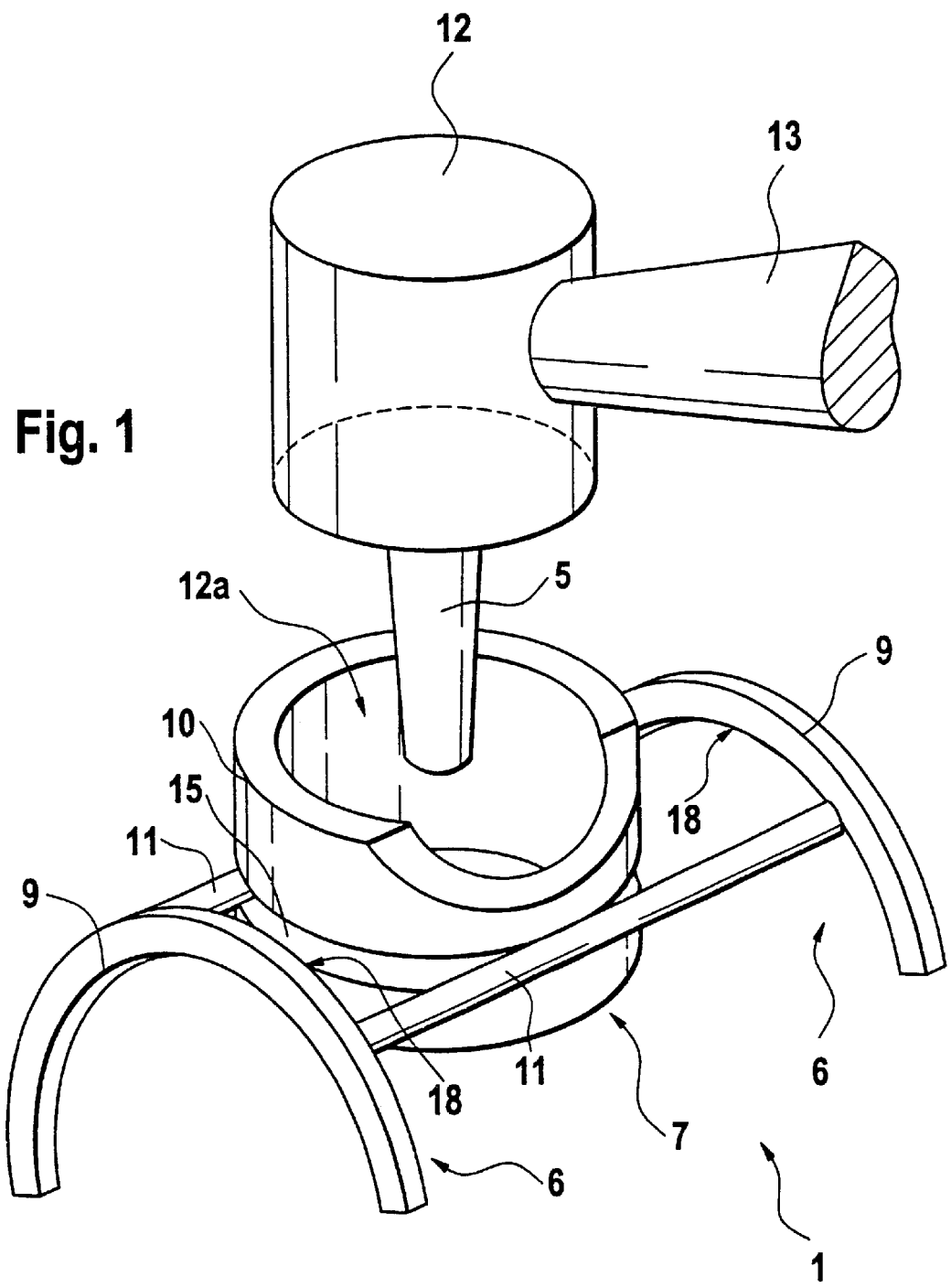
FIG. 1 a view of a device to treat the neighboring teeth of a gap for placement of a dental bridge, wherein the tool head holding the treatment tool is pulled out from the positioning device.

A device, identified in its entirety as 1, to treat the neighboring teeth 2 of a gap 3 to place a dental bridge 4 as a replacement for a lost tooth is provided. The device has a rotating grinding tool used as a treatment tool 5 to remove tooth material. The device has a mounting fixture 6 that can be fastened to the patient's teeth and that contains an adjustable positioning device 7 to position the treatment tool 5. Using the positioning device 7, the treatment tool 5 can be moved toward the neighboring teeth 2 back and forth to make recesses 8 in the lateral walls of the neighboring teeth 2 facing the gap 4.

Figure 3:
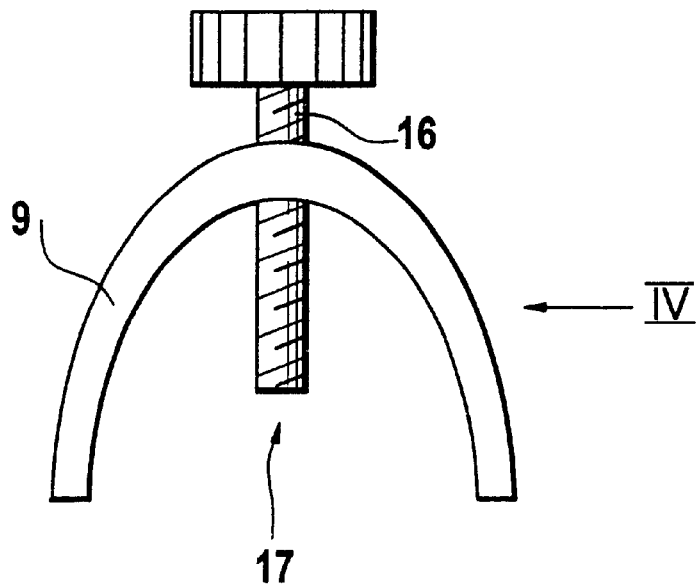
FIG. 3 is a side view of a U-shaped holder to fasten the positioning device to the patient's teeth.
Figure 4:
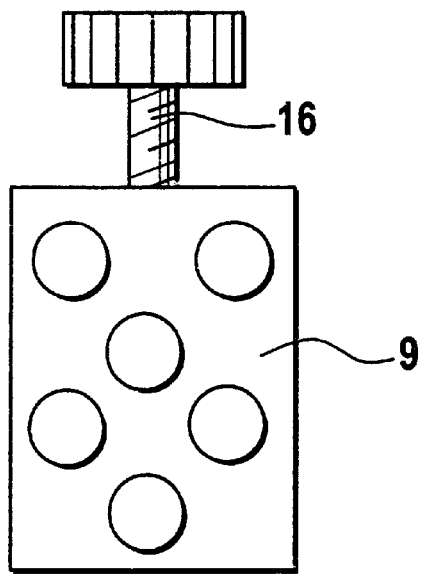
FIG. 4 is a side view of the holder from the direction indicated in FIG. 3.

In FIGS. 3 and 4, it can be seen that the mounting fixture 6 has two U-shaped holders 9 in the form of a fork (FIG. 5) that each grasp one of the two neighboring teeth 2 adjacent to the gap 4. One of the two U-shaped sides of the holders 9 is located at the inner lateral surface and the other is located at the outer lateral surface of its associated neighboring tooth 2. The transition area between the U-crossbar and the U-sides of the holders 9 are rounded. The opening width between the U-sides of the holders 9 decreases as it goes from the free ends of the U-sides toward the U-crossbar, preferably continuously.

The fastening of the holders 9 to the neighboring teeth 2 is done using a compound that solidifies. Prior to placing the holders 9 onto the neighboring teeth 2, this compound is applied in a doughy, paste-like or viscous state to the inside of the holders 9. Afterward, the holders 9 coated with the compound are placed onto the neighboring teeth 2, wherein the compound comes into contact with the neighboring teeth 2 and fills in the intermediate spaces between the holders 9 and the neighboring teeth 2. The compound then solidifies in the oral cavity of the patient so that the mounting fixture is solidly connected to the neighboring teeth 2. The compound preferably still has a certain amount of elasticity so that the mounting fixture 6 can be pulled off of the patient's teeth in a simple manner after the treatment of the neighboring teeth. So that the compound adheres more to the holders 9 when the mounting fixture 6 is pulled off, the holders 9 have holes in them into which the compound penetrates when it is applied to the holders 9 (FIG. 4).

As can be seen especially clearly in FIG. 1, the positioning device 7 has a sliding guide with a sled 10 that shifts relative to the mounting fixture 6. The sled 10 is mounted to guide rails 11 that run parallel to one another and that are each connected at their ends to one of the two holders 9 located in the working position on both sides of the gap 4.

Figure 5:
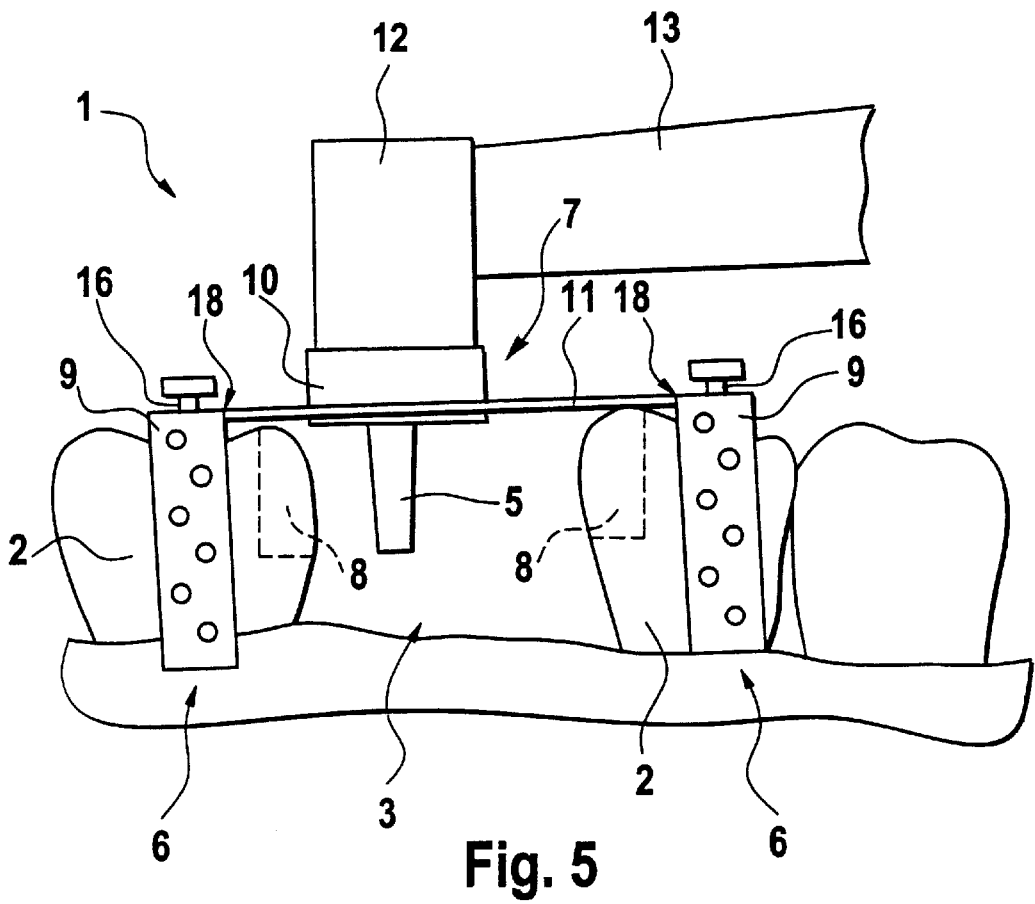
FIG. 5 is a side view of the device according to FIG. 1 and shown in FIG. 2 fastened to the patient's teeth.
Figure 6:
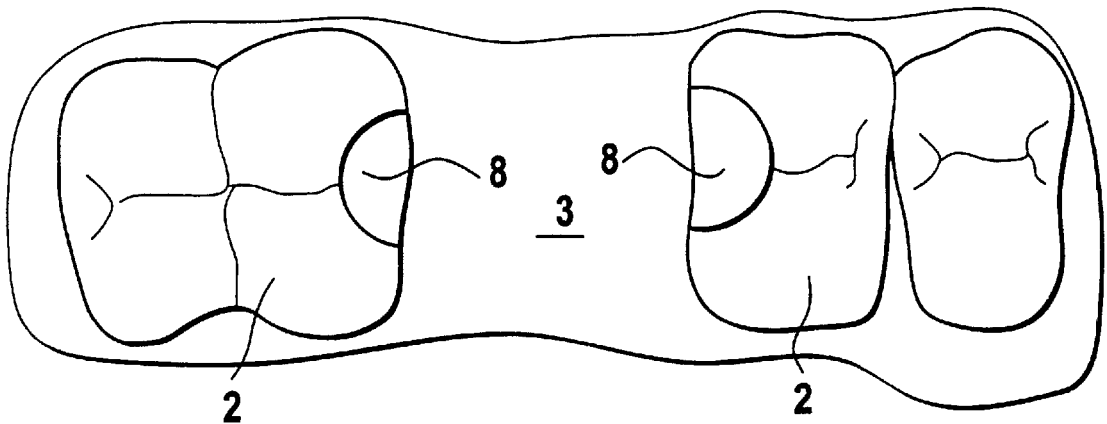
FIG. 6 is a view of the teeth adjacent to the gap to be closed by the dental bridge after making the recesses for the anchor protrusions of the dental bridge.

The guide rails 11 are located in the working position in a plane that runs approximately parallel to the plane of the chewing surfaces of the neighboring teeth 2 or is identical with it (FIG. 5). The sled 10 is located between the holders 9 and can move toward and away from the neighboring teeth 2 parallel to the guide rails 11 on the holders 9 in order to make the recesses 8 into them. In FIG. 5, it can be seen that the holders 9 are located outside the recesses 8 to be made in the neighboring teeth 2 so that the treatment tool 5 to remove the tooth material can be shifted into the recesses 8.

The treatment tool 5 is located on a known tool head 12 of dental treatment equipment. The treatment equipment has a grip 13, shown in the figure only partially, in which a drive motor is located that drives the treatment tool 5. The end of the grip 13 opposite the tool head 12 is connected to a power supply line and if necessary a water supply line to feed cooling water to the treatment tool 5. The tool head 12 is designed as an angled head and its end is at an approximately 90° angle with respect to the grip 13.

Figure 2:
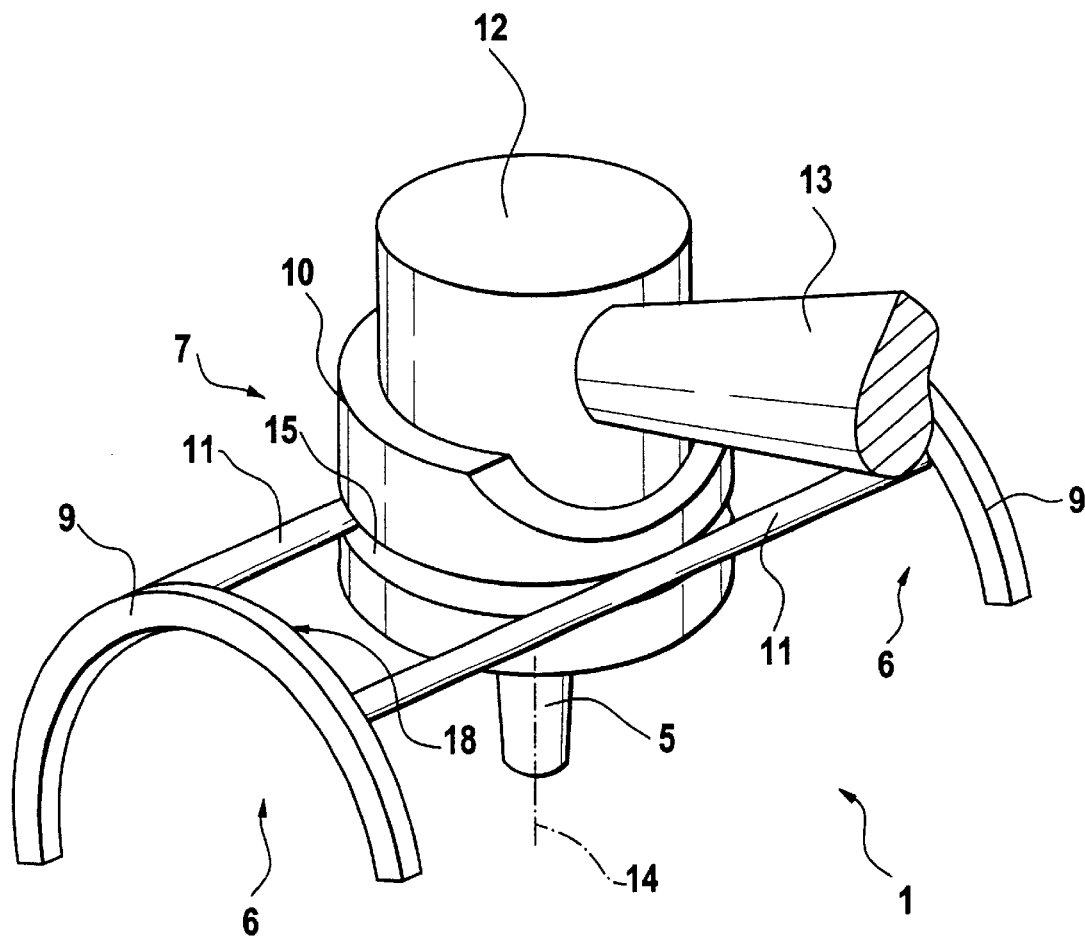
FIG. 2 is a representation similar to FIG. 1, wherein the tool head is inserted into the sled of the positioning device.

It can be seen in FIGS. 1 and 2 that the tool head 12 can be connected removably to the sled 10 of the sliding guide. The sled 10 has in addition a receptacle 12a adjusted to fit the exterior contour of the tool head 12 and designed as a recess. The end of the tool head 12 facing the treatment tool 5 can be placed form-fit into this recess. Therefore, the receptacle 12a and the tool head 12 placed into it form a press fit that enables a solid grip of the tool head 12 in the receptacle 12a. Overall, therefore, the tool head 12 and the sled 10 and the receptacle 12a form a plug coupling whose coupling parts can be connected together and are removable. This lets the relatively expensive tool heads 12 already in existence in dental practice be combined with the positioning device 7 and thus to continue to be used. Of course, the device 1 can also have its own drive system independent of existing equipment for the treatment tool 5, which is preferred to be a micro-drive unit located directly at the sled 10.

The treatment tool 5 located at the tool head 12 is rotated about a rotational axis 14 that runs perpendicular to the direction of extension of the grip 13. This is labeled in FIG. 2 as dashed line. The tool head 12 placed into the receptacle 12a of the sled 10 is connected to the holder 9 and pivots about the rotational axis 14 of the treatment tool 5 relative to the holder. The guide rails 11 located laterally on both sides of the sled 10 engage a common annular notch 15 at the external perimeter of the sled 10 in such a way that the sled 10 and the tool head 12 held in it can be slid on the one hand along the guide rails 11 and on the other hand can be pivoted about the rotational axis relative to the guide rails 11. The grip 13 can in this way be titled inside the oral cavity of the patient to a good position accordingly. In this manner, the tilt position of the grip 13 can even be changed as the tool head 12 is slid by the sled 10, if necessary, in order to attain good accessibility to the respective treatment position.

In FIG. 5, it can be seen that there is a spacing element 16 located at each of the U-shaped holders 9 having a point of support 17 for the neighboring teeth 2 that can be shifted perpendicular to the plane of the chewing surface of the neighboring teeth 2. The point of support 17 is located at the free end of an adjustment screw that penetrates the U-cross beam of the holder 9 approximately in the direction that its U-sides extend. Each of the adjustment screws has a screw head at its end opposite the point of support 17 that has a grip for a rotating tool or can be adjusted by hand, in particular using a knurled edge provided at the exterior perimeter of the screw head. Using the adjustment screws, the height and/or the tilt of the plane spanned by the guide rails 11 can be adjusted relative to the plane of the chewing surfaces of the teeth. In this way, it is possible, in particular, to adjust the mounting fixture 6 to different tooth heights, for example if one of the two ends of the mounting fixture 6 is to be fastened to a molar and the other end is to be fastened to an eye tooth.

To make the treatment tool 5 slide using the positioning device 7 about an exactly defined path length, stops 18 are provided at the holders 9 on both sides of the sled 10, with respect to which the sled 10 can be positioned. In this way, this path length is adjusted according to the length of the dental bridge 4 such that the distance between the lateral surfaces of the recesses 8 of the two neighboring teeth 2 located on both sides of the gap 3 corresponds to the dental bridge 4 and its anchor protrusions 19. In this way, independent of the geometric dimensions of the gap 3 and the neighboring teeth 2, it is ensured that the dental bridge 4 can be exactly placed into the intermediate space formed between the recesses 8.

Below, the work steps required to install the dental bridge 4 are explained briefly. First, the holders 9 of the device 1 are fastened to the neighboring teeth 2 of the gap 3. Then, the tool head 12 containing the treatment tool 5 is placed into the receptacle 12a of the sled 10 and connected to it in a form-fitting manner. Then, the treatment tool is rotated about the axis 14 and moved forward until the sled 10 lies against the stop 18 in order to make each of the recesses 8 in the neighboring teeth 2. When both recesses have been produced, the device 1 is removed from the patient's teeth. Then, the pre-manufactured dental bridge 4 is placed in the gap 3, wherein the anchor protrusions 19 engage into the recesses 8. Cement, adhesive or a similar fastening and/or sealing agent is applied to any remaining gaps between the anchor protrusions 19 and the recesses 8. After the sealing agent has hardened or has solidified, the surfaces of the anchor protrusions and/or the adjacent areas of the neighboring teeth 2 still visible can be ground down if needed in order to adjust the form of the anchor protrusions 19 to that of the neighboring teeth 2 and in particular to attain a continuous, smooth transition between the neighboring teeth 2 and the anchor protrusions 19. If necessary, the chewing surface of the bridge section 20 can also be ground in order to improve occlusion.

Figure 7:
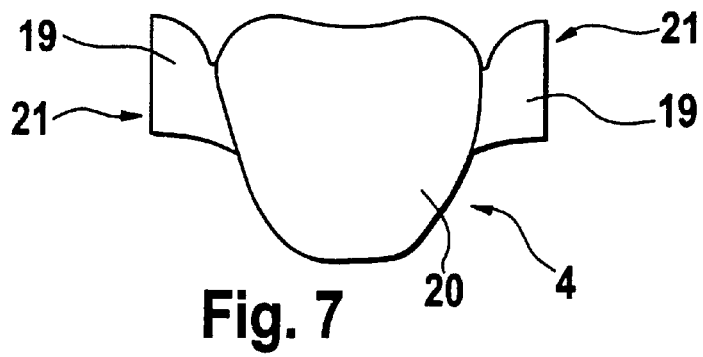
FIG. 7 is a side view of the dental bridge with the illustrated anchor protrusions.
Figure 8:
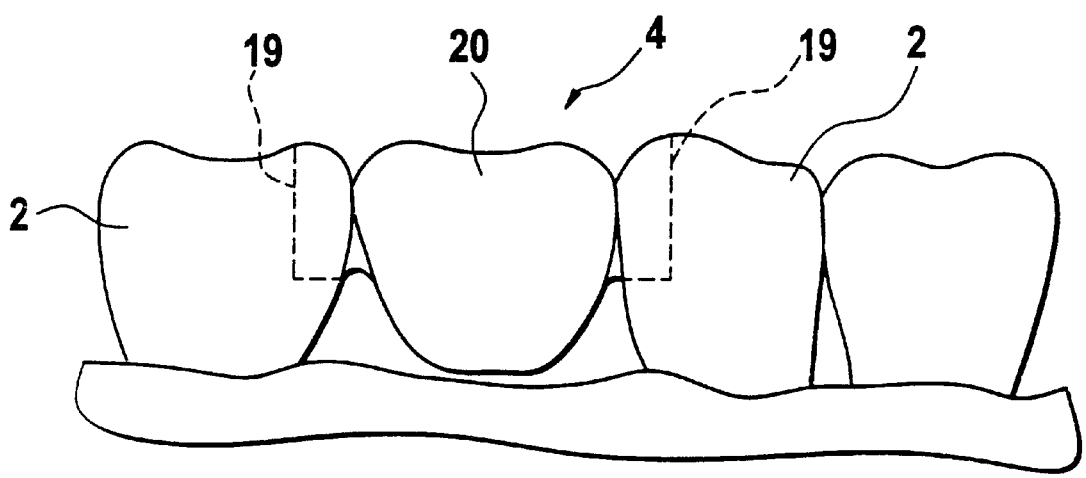
FIG. 8 is a side view of the dental bridge placed in the gap, wherein the anchor protrusions hidden by the neighboring teeth are shown in dashed lines.
Figure 9:
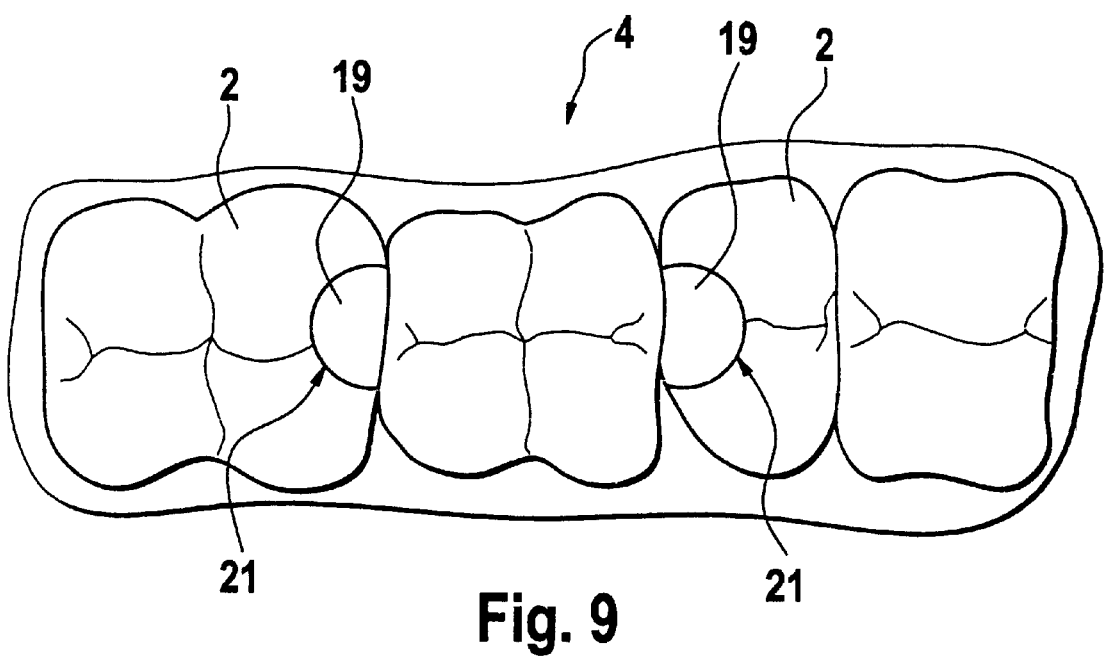
FIG. 9 is a view of the dental bridge placed into the gap wherein the neighboring teeth are also recognizable.

The device 1 to treat the neighboring teeth 2 of the gap 3 is a part of a kit to make a dental bridge. The kit has a number of pre-manufactured dental bridges 4 that each has a bridge section 20 with at least one synthetic tooth that replaces the missing tooth (teeth) of the gap 3. As can be seen in FIG. 7, on both sides of the bridge section 20 there is an anchor protrusion 19 in the direction of extension with the prescribed dimensions. In FIG. 8 and 9, it can be seen that the dimensions of the anchor protrusions 19 fit with those of the recesses 8 so that the anchor protrusions 19 of the dental bridge 4 placed into the gap 3 directly abut the neighboring teeth 2 or are only separated from them by a small gap. In the gap, depending on the material and type of dental bridge, a cement or adhesive material can be applied in known fashion when the dental bridge 4 is placed. After solidification of the adhesive or the cement, the dental bridge 4 is then solidly connected to the neighboring teeth. In FIGS. 7 and 9, it can be seen that the anchor protrusions 19 located on both sides of the bridge section 20 have the same dimensions as prescribed by the dimensions of the treatment tool 5.

The treatment tool 5 has the form of a truncated cone that narrows as it goes from the tool head 12 to the free end of the treatment tool 5. The lateral abutting surfaces 21 of the anchor protrusions 19 opposite the bridge section 20 are each located on the outer surface of a truncated cone matching the form of the treatment tool 5. This truncated cone narrows as it goes from the chewing surface of the bridge section 20 to the rear side of the bridge section 20 that is opposite to it. The angle at a diameter plane of the cone that the outer cone surface makes with a line parallel to the axis of the cone is preferred to measure between 0 and 6°. By means of the outer cone surfaces provided at the anchor protrusions 19 and the surfaces of the matching recesses 8 facing them in the working position, an improved adhesion of the anchor protrusions 19 to the neighboring teeth 2 is attained.

It should be mentioned that the lateral abutting surfaces 21 of the anchor protrusions 19 of the dental bridge 4 have a surface roughness and in particular can be sand-blasted so that a silicon layer coated on it can better adhere to it. This is applied onto the lateral abutting surfaces 21 of the anchor protrusions 19 by the dentist shortly before placement of the dental bridge 4.

The device 1 to treat the neighboring teeth 2 of a gap 3 for the placement of dental bridge that replaces at least one tooth has a treatment tool 5 to remove tooth material, in particular a grinding tool. The device 1 has a mounting fixture 6 to fasten to the patient's teeth. This mounting fixture contains an adjustable positioning device 7 for guided positioning of the treatment tool. The treatment tool can be moved toward and away from the neighboring teeth 2 using the positioning device 7 to make recesses 8 in the sides of the neighboring teeth 2 facing the gap 3.

What is claimed is:

1. A combination of a device (1) to treat neighboring teeth (2) adjacent to a gap (3) for placement of a dental bridge (4) that replaces at least one missing tooth and a pre-manufactured dental bridge, the device comprising:

a treatment tool (5) to remove tooth material and a mounting fixture (6) that can be fastened to the patient's teeth, the mounting fixture (6) includes guide rails (11) and at least two holder sections connected together by the guide rails that are located on opposite sides of the treatment tool (5), with each of the holder sections being adapted to be fastened to at least one tooth, and an adjustable positioning device (7) to position the treatment tool (5) having a sliding guide with a sled (10) is located on and slides along the guide rails (11) to guide the treatment tool (5), the mounting fixture (6) is adapted to be fastened to teeth located on both sides of the gap (3) so that the treatment tool (5) can be moved by sliding the adjustable positioning device (7) along the guide rails (11) toward or away from the neighboring teeth (2) to make recesses (8) in sides of the neighboring teeth (2) facing the gap (3), and stops (18) are provided on the mounting fixture (6) at a predetermined distance apart on both sides of the sled (10) to define a path length of the treatment tool (5) in a direction of movement of the sled (10) so that the path length including the gap and the recesses has a predetermined size; and the pre-manufactured dental bridge includes a bridge section (20) and an anchor protrusions (19) on each side of the bridge section that correspond to the recesses, and the pre-manufactured dental bridge has a length that corresponds to the predetermined size.

2. The combination according to claim 1, wherein the anchor protrusions (19) located on the sides of the bridge section (20) have at least one equal dimension.

3. The combination according to claim 1, wherein an abutting surface (21) of each of the anchor protrusions (19) opposite the bridge section (20) has one of a cylindrical surface or an outer conical surface of a truncated cone that narrows from a chewing surface toward a base of the bridge section.

4. The combination according to claim 1, wherein at least one anchor protrusion (19) is formed by a free end of a locking pin placed in a hole in the dental bridge (4).

5. The combination according to claim 1, wherein at least one anchor protrusion (19) is formed in one piece with the bridge section.

6. The combination according to claim 1, further comprising a number of pre-manufactured dental bridges (4) having synthetic teeth having at least one of different colors, different materials and different dimensions.

\* \* \* \* \*